(12) United States Patent
Sparks et al.

(10) Patent No.: US 9,039,976 B2
(45) Date of Patent: May 26, 2015

(54) MEMS SENSORS WITH CLOSED NODAL ANCHORS FOR OPERATION IN AN IN-PLANE CONTOUR MODE

(75) Inventors: Andrew Sparks, Cambridge, MA (US); William D. Sawyer, Arlington, MA (US)

(73) Assignee: Analog Devices, Inc., Norwood, MA (US)

( * ) Notice: Subject to any disclaimer, the term of this patent is extended or adjusted under 35 U.S.C. 154(b) by 204 days.

(21) Appl. No.: 13/017,247

(22) Filed: Jan. 31, 2011

(65) Prior Publication Data

US 2012/0195797 A1    Aug. 2, 2012

(51) Int. Cl.
*G01N 29/02*    (2006.01)
*G01N 29/036*   (2006.01)
*H03H 9/10*     (2006.01)
*H03H 9/02*     (2006.01)

(52) U.S. Cl.
CPC ............ *G01N 29/022* (2013.01); *G01N 29/036* (2013.01); *G01N 2291/02818* (2013.01); *G01N 2291/0427* (2013.01); *H03H 9/1057* (2013.01); *H03H 2009/02503* (2013.01)

(58) Field of Classification Search
CPC ..... G01N 29/002; G01N 29/02; G01N 29/00; G01N 29/036; H03H 9/1057; H03H 9/10; H03H 9/00
USPC ................................. 422/88, 83, 50
See application file for complete search history.

(56) References Cited

U.S. PATENT DOCUMENTS

| | | | |
|---|---|---|---|
| 4,809,589 A | 3/1989 | Bertrand | 92/98 R |
| 5,177,579 A | 1/1993 | Jerman | 73/724 |
| 5,589,082 A | 12/1996 | Lin et al. | 216/2 |
| 5,750,899 A | 5/1998 | Hegner et al. | 73/756 |
| 5,937,275 A | 8/1999 | Munzel et al. | 438/50 |
| 5,992,233 A | 11/1999 | Clark | 73/514.35 |
| 6,635,509 B1 | 10/2003 | Ouellet | 438/106 |
| 6,892,575 B2 | 5/2005 | Nasiri et al. | 73/504.12 |
| 6,985,051 B2 | 1/2006 | Nguyen et al. | 333/186 |
| 7,032,451 B2 | 4/2006 | Geen | 73/504.14 |
| 7,051,590 B1 | 5/2006 | Lemkin et al. | 73/504.04 |
| 7,178,378 B2 | 2/2007 | Crawley et al. | 73/24.06 |
| 7,427,819 B2 | 9/2008 | Hoen et al. | 310/320 |
| 7,492,241 B2 | 2/2009 | Piazza et al. | 333/189 |
| 7,551,043 B2 | 6/2009 | Nguyen et al. | 333/186 |

(Continued)

FOREIGN PATENT DOCUMENTS

| | | | |
|---|---|---|---|
| EP | 1788385 | 5/2007 | G01N 29/02 |
| EP | 2216904 | 8/2010 | H03H 9/25 |
| WO | WO 2009/066640 | 5/2009 | H03H 9/25 |

OTHER PUBLICATIONS

Bill Drafts, "Acoustic Wave Technology Sensors," Sensors (www.sensorsmag.com), 8 pages, Oct. 1, 2000.

(Continued)

*Primary Examiner* — Christine T Mui
(74) *Attorney, Agent, or Firm* — Sunstein Kann Murphy & Timbers LLP

(57) ABSTRACT

A MEMS sensor includes at least one closed nodal anchor along a predetermined closed nodal path on at least one surface of a resonant mass. The resonant mass may be configured to resonate substantially in an in-plane contour mode. Drive and/or sense electrodes may be disposed within a cavity formed at least in part by the resonant mass, the closed nodal anchor, and a substrate.

23 Claims, 18 Drawing Sheets

(56) References Cited

U.S. PATENT DOCUMENTS

| | | | |
|---|---|---|---|
| 2003/0119220 A1 | 6/2003 | Mlcak et al. | 438/52 |
| 2003/0183888 A1 | 10/2003 | Bar-Sadeh et al. | 257/419 |
| 2004/0051595 A1 | 3/2004 | Yoshimine et al. | 331/158 |
| 2005/0148065 A1 | 7/2005 | Zhang et al. | 435/287.2 |
| 2006/0133953 A1 | 6/2006 | Zhang et al. | 422/58 |
| 2006/0196253 A1 | 9/2006 | Crawley et al. | 73/53.01 |
| 2006/0237806 A1 | 10/2006 | Martin et al. | 257/415 |
| 2007/0046398 A1 | 3/2007 | Nguyen et al. | 333/186 |
| 2007/0172940 A9 | 7/2007 | Manalis et al. | 435/287.2 |
| 2008/0190181 A1 | 8/2008 | Khuri-Yakub et al. | 73/64.53 |
| 2008/0282833 A1 | 11/2008 | Chaumet | 74/5 R |
| 2009/0114016 A1 | 5/2009 | Nasiri et al. | 73/504.12 |
| 2009/0173158 A1 | 7/2009 | Gehring | 73/590 |
| 2009/0277271 A1* | 11/2009 | Seppa et al. | 73/627 |
| 2010/0263445 A1 | 10/2010 | Hayner et al. | 73/504.12 |
| 2011/0192226 A1 | 8/2011 | Hayner et al. | 73/504.12 |
| 2012/0111112 A1 | 5/2012 | Sammoura et al. | 73/514.01 |
| 2012/0111113 A1 | 5/2012 | Sammoura et al. | 73/514.01 |
| 2012/0112765 A1* | 5/2012 | Sparks et al. | 324/633 |

OTHER PUBLICATIONS

Marc-Alexandre Dubois, "Thin film bulk acoustic wave resonators: a technology overview," MEMSWAVE 03, Toulouse, France, 4 pages, Jul. 2-4, 2003.

Saukoski, "System and Circuit Design for a Capacitive MEMS Gyroscope," Doctoral Dissertation, TKK Dissertations 116, Helsinki University of Technology, 279 pages. (2008).

International Searching Authority, International Search Report, International Application No. PCT/US2012/023212, dated Apr. 11, 2012, together with the Written Opinion of the International Searching Authority, 11 pages.

* cited by examiner

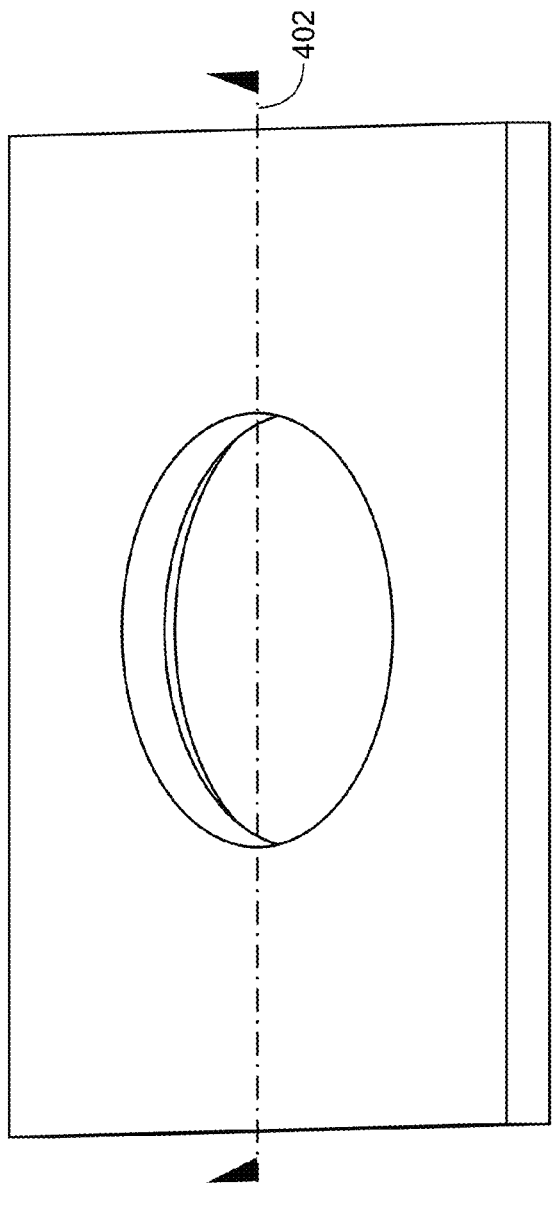
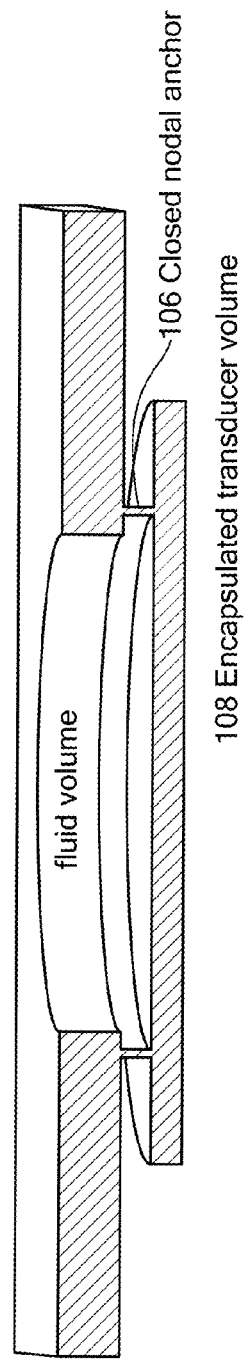
*FIG. 4A*
*FIG. 4B*

MEMS SENSORS WITH CLOSED NODAL ANCHORS FOR OPERATION IN AN IN-PLANE CONTOUR MODE

CROSS-REFERENCE TO RELATED APPLICATION(S)

The subject matter of this patent application may be related to the subject matter of U.S. patent application Ser. No. 12/853,619 entitled MEMS IN-PLANE RESONATORS filed on Aug. 10, 2010, which claims the benefit of U.S. Provisional Patent Application No. 61/233,581 entitled MEMS IN-PLANE RESONATORS filed on Aug. 13, 2009. Each of these patent applications is hereby incorporated herein by reference in its entirety.

FIELD OF THE INVENTION

The present invention relates generally to MEMS devices and, in particular, to MEMS in-plane resonators.

BACKGROUND OF THE INVENTION

Sensors based of mechanically resonant elements have long been of interest due to their high sensitivity and electrical readout capability. Resonant sensors allow the use of resonant frequency and/or quality factor (Q) to detect such things as mass, stiffness, and/or damping changes at the resonator surfaces. Applications for such sensors are broad and include, among other things, inertial, pressure, temperature, strain, flow rate, viscosity, density, and chemical/biological sensors.

Many of these sensors are currently constructed from quartz or other piezoelectric materials. Although their performance is proven, they are difficult to miniaturize, integrate, and optimize in a high-volume wafer fabrication process, such as that commonly used to make silicon-based integrated circuits.

A major limitation of resonant sensors exposed to a non-vacuum environment is the performance degradation from viscous damping through various physical mechanisms. The damping directly lowers the Q and therefore the detection limits of the device.

One way that the piezoelectric community has addressed this performance degradation is by constructing crystals with shear (in-plane) vibration modes. Analogous to rowing a boat with the edge of an oar instead of the face, much less force is exerted by the fluid on the mechanical element (and vice versa), and therefore the damping can be minimized. Piezoelectric materials include metal electrodes on two sides for transduction, so placing them in liquids or harsh gaseous environments can require sophisticated passivation or packaging strategies, which can affect both performance and cost. Capacitive transduction, which is favored among non-piezoelectric micromechanical resonators for its simplicity and sensitivity, would also be adversely affected by the presence of fluid or changing environmental conditions. Other transduction methods have their own drawbacks related to cost, performance, interfacing with the sense environment, and/or integration.

There is considerable effort in the MEMS industry to manufacture MEMS resonators (typically silicon) to create oscillators and filters that would compete with conventional quartz devices. However, these devices generally require that all resonator surfaces be packaged in a vacuum with no external environmental exposure. Sealing of these devices can be achieved by capping at low pressures.

Some exemplary efforts to commercialize biosensors based on microscale resonators include piezoelectric devices (e.g., BioScale, Inc. U.S. Pat. No. 07178378, US2006/0196253, Boston Microsystems US2003/0119220, and Intel US2006/0133953) that require exotic materials (compared to silicon) and passivation schemes, and microchannel resonators (e.g., MIT/Affinity Biosensors, US2007/0172940) that require all fluids of interest to flow through a micron-scale resonant channel that provides a natural isolation of the fluid but adds a requirement of microfluidic flow control.

The pressure sensor community demonstrated corrugated diaphragms with isolated capacitive transduction as early as the 1980s (e.g., U.S. Pat. No. 5,750,899, US2003/0183888, U.S. Pat. Nos. 4,809,589, 5,177,579), but these devices move out-of-plane and therefore generally would suffer from overwhelming damping in fluid environments.

Likewise, capacitive micromachined ultrasonic transducers (CMUTs), which resonate in out-of-plane flexural modes, have been used for gas sensing and proposed for liquid sensing (e.g., Stanford University, US2008/0190181) but generally have similar damping limitations.

"In-situ capping" is currently being pursued by several companies to hermetically seal MEMS devices at the wafer scale (e.g., SiTime, in collaboration with Bosch, in an effort to build all-vacuum-encapsulated resonators). Some of the in-situ capping patents in public domain include U.S. Pat. No. 6,635,509 filed by Dalsa Semiconductors, U.S. Pat. No. 5,589,082 filed by University of California Regents, and U.S. Pat. No. 5,937,275 filed by Bosch. Also a European Government sponsored project SUMICAP had some work done on this aspect. However, in the above literature, the main purpose has been to provide a rigid cap to the devices to act as protection.

Resonators have been used for biological/chemical sensing, viscometry, and similar applications. For example, the quartz crystal microbalance (QCM) was demonstrated as a mass sensor in 1959. Since then, it has become a common analytical tool in the chemical and biological sciences for use in vacuum, gas, and liquid environments. Typically, such sensors are relatively large (e.g., centimeters across by hundreds of microns thick), and this relatively large size tends to limit their mass resolution. However, QCM is a pervasive laboratory tool for biosensing, chemical sensing, viscometry, etc.

Silicon-based lateral resonators for liquid applications have been demonstrated utilizing piezoresistive detection without isolating part of the device from the liquid such that the devices may be susceptible to particles that can be trapped under the resonant mass. Robust passivation of piezoresistors is also a significant reliability concern with these devices.

A lateral resonator with exposed electrodes is described in U.S. Pat. No. 7,551,043 filed by Nguyen et al.

An example of prior art targeting frequency reference applications is Nguyen and Xie (U.S. Pat. No. 6,985,051), which utilizes contour modes in silicon with capacitive transduction. In this example, there is no need to isolate any regions of the resonant structure's surface. Similarly, Piazza, Stephanou & Pisano (U.S. Pat. No. 7,492,241), a piezoelectric resonator implementation, is also not designed for partial encapsulation.

Each of the above-referenced patents and published patent applications is hereby incorporated herein by reference in its entirety.

SUMMARY OF THE INVENTION

A MEMS sensor includes at least one closed nodal anchor along a predetermined closed nodal path on at least one surface of a resonant mass. The resonant mass may be configured to resonate substantially in an in-plane contour mode. Drive and/or sense electrodes may be disposed within a cavity formed at least in part by the resonant mass, the closed nodal anchor, and a substrate.

In accordance with one aspect of the invention there is provided a MEMS sensor comprising a substrate; a resonant mass configured to resonate in an in-plane contour mode; a first closed nodal anchor connecting the resonant mass to the substrate along a first predetermined closed nodal path on a first surface of the resonant mass; and at least one transducer in communication with the first resonant mass for at least one of driving and sensing in-plane movement of the resonant mass, wherein at least a portion of the first surface of the resonant mass is configured for exposure to an external environment.

In various alternative embodiments, the at least one transducer (e.g., a capacitively-coupled transducer or a piezoelectrically-coupled transducer) may be at least partially contained within a cavity formed at least in part by the resonant mass, the substrate, and the first closed nodal anchor. The cavity may be partially or completely evacuated or may be filled with a gas or other substance. The MEMS sensor may include a second closed nodal anchor connecting the resonant mass to the substrate along a second predetermined closed nodal path on a second surface of the resonant mass opposite the first surface. The resonant mass may be part of a cap that is attached to a substrate wafer to form thereby an isolated cavity within which the at least one transducer is at least partially contained. The resonant mass may be movably coupled to the at least one transducer via an elastic material, and portions of the at least one transducer that would otherwise be exposed to the external environment may be covered with at least one material to isolate those portions from the external environment. The at least one transducer may include at least one drive transducer and at least one sense transducer, wherein the at least one drive transducer may be operatively coupled to a side edge of the resonant mass and the at least one sense transducer may be operatively coupled to a bottom surface of the resonant mass, the transducers isolated from the external environment. The MEMS sensor may include a set of shield structures on the substrate wafer. The resonant mass may be movably coupled by a suspension, such as an elastic plug.

The portion of the first surface configured for exposure to the external environment may be at least partially covered by a material meant to interact with a specific type of target in the external environment, such interaction changing the moving mass of the resonant mass so as to change the resonance frequency of the resonant mass, and the sensor may further include circuitry configured to detect a change in resonance frequency resulting from such interaction. The material may include, for example, an adhesive material to which the target adheres, a chemically or electrochemically active material, a hydrophilic material, a receptor material to which a specific target binds, and/or a material that dissolves or dissipates in the presence of the target so as to decrease the moving mass of the resonator and consequently increase the resonance frequency of the resonator.

Additionally or alternatively, the portion of the first surface configured for exposure to the external environment may be at least partially covered by a material meant to reduce interactions with the external environment.

Additionally or alternatively, the resonant mass may include raised and/or recessed features patterned or otherwise formed on of from the top surface of the resonant mass.

Additionally or alternatively, the MEMS sensor may include at least one of a microfluidic network and sensors.

In various embodiments, the MEMS sensor may include or may be used in conjunction with circuitry for driving resonance of the resonant mass, sensing resonance of the resonant mass including sensing any changes in resonant frequency (e.g., caused by interaction of the resonant mass with the environment), applying a predetermined electrical potential to at least one outer conductive surface exposed to the external environment, and/or sensing an electrical potential caused by interaction with the external environment.

In accordance with another aspect of the invention there is provided a MEMS sensor comprising a substrate; a plurality of resonant masses, each resonant mass configured to resonate in an in-plane contour mode and including a first closed nodal anchor connecting the resonant mass to the substrate along a first predetermined closed nodal path on a first surface of the resonant mass; and a plurality of transducers in communication with the resonant masses for at least one of driving and sensing in-plane movement of the resonant masses, wherein at least a portion of the first surface of each resonant mass is configured for exposure to an external environment.

In various alternative embodiments, the plurality of transducers may be at least partially contained within a cavity formed at least in part by the resonant masses, the substrate, and the first closed nodal anchors. Each resonant mass may further comprise a second closed nodal anchor connecting the resonant mass to the substrate along a second predetermined closed nodal path on a second surface of the resonant mass opposite the first surface. The portions of the first surfaces configured for exposure to the external environment may be at least partially coated with the same material or may be at least partially coated with different materials. The resonant masses may be mechanically coupled.

In accordance with another aspect of the invention there is provided an array of MEMS sensors having closed nodal anchors.

In various alternative embodiments, at least two sensors are of the same mechanical design; at least two sensors are of different mechanical designs; at least two sensors have the same functional coating; at least two sensors have different functional coatings; and/or at least two sensors are electrically coupled.

In accordance with another aspect of the invention there is provided a method of fabricating a MEMS in-plane resonator comprising forming a resonant mass supported by a substrate and configured to resonate substantially in an in-plane contour mode; forming a first closed nodal anchor connecting the resonant mass to the substrate along a first predetermined closed nodal path on a first surface of the resonant mass; and forming at least one transducer in communication with the first resonant mass for at least one of driving and sensing in-plane movement of the resonant mass, wherein at least a portion of the first surface of the resonant mass is configured for exposure to an external environment.

BRIEF DESCRIPTION OF THE DRAWINGS

The foregoing and advantages of the invention will be appreciated more fully from the following further description thereof with reference to the accompanying drawings wherein:

FIG. 4A schematically shows a top perspective view and FIG. 4B schematically shows a cross-sectional side view of a device having a circular disk resonant mass (excluding electrodes), in accordance with an exemplary embodiment of the present invention;

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Figure 1A:
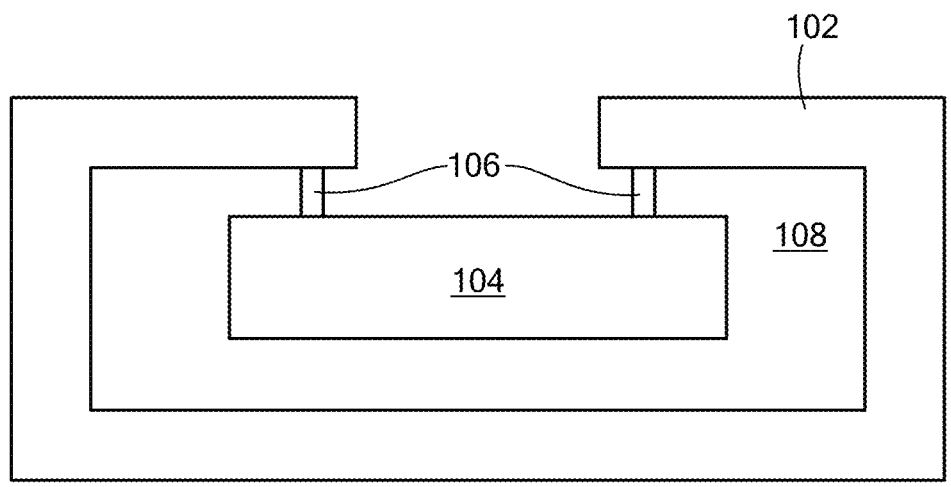
FIG. 1 schematically shows two anchoring strategies in accordance with exemplary embodiments of the present invention, where FIG. 1A schematically shows a cross-sectional side view of a device anchored at the fluid-contacting surface and FIG. 1B schematically shows a cross-sectional side view of a device anchored from both sides.

Definitions. As used in this description and the accompanying claims, the following terms shall have the meanings indicated, unless the context otherwise requires:

A "set" includes one or more members.

The term "in-plane" should be understood to mean predominately in the plane of the resonant mass. Typically, a small amount of out-of-plane motion will be present, for example, due to the Poisson effect, fabrication variations, etc., and generally can be tolerated.

The "mode" of a resonating body is the shape of motion of the body at resonance.

An "electrode" is a structure through which an electrical or electromechanical effect is applied and/or sensed. In exemplary embodiments, various electrodes are used for applying and/or sensing electrical or electromechanical effects through capacitive coupling (e.g., between a resonant mass and one or more adjacent structures), although it should be noted that other types of electrodes and couplings may be used (e.g., piezoelectric). Thus, in exemplary embodiments, electrodes may include a resonant mass and one or more structures for driving and/or sensing movement of the resonant mass.

A structure may be "attached" to another structure by being directly or indirectly formed on or bonded to the other structure. Thus, for example, a cap may be attached to a wafer by being formed directly or indirectly on the wafer in situ (e.g., using MEMS processes of depositing, patterning, and etching materials) or a cap may be attached to a wafer by being bonded directly or indirectly to the wafer.

In embodiments of the present invention, a resonator is configured to operate in a type of bulk acoustic wave (BAW) resonant mode called a contour mode in which the mode shape and frequency do not depend (to first order) on the thickness of the device, only on the lateral shape, lateral dimensions, and material properties. Thus, the mode shape can be described by a two-dimensional contour plot or the corresponding equations. For example, a circular disk has radial contour modes (sometimes called breathing modes) when the disk radially expands and contracts.

Embodiments of the present invention employ contour modes with closed nodal paths. A node is strictly defined as a point of the contour with zero displacement. A closed nodal path is a curve that can be drawn on the contour such that all points on the line are nodes and the curve forms a closed loop. Since node locations vary somewhat with manufacturing and not all shapes have closed paths of zero displacement, the definition of closed nodal paths is generalized herein to include those which have small displacements relative to the point of maximum displacement of the resonant structure (i.e., defined by local minima in displacement).

Since points along the closed nodal path have little or no displacement when the contour mode of interest is excited, the loop becomes an ideal location to anchor the resonant mass to a substrate. Because the nodal loop is closed, this anchoring effectively splits the volume surrounding the resonant mass into two isolated volumes, but both volumes are in contact with parts of the resonant structure with finite displacement so one volume can be used for mechanical sensing and the other can be used for electrical drive and sense. For convenience, an anchor placed along this nodal loop (within misalignment tolerances) is referred to herein as a closed nodal anchor. Generally speaking, the closed nodal anchor should be as narrow as possible since the true nodal path is infinitely thin. The closed anchor is generally only needed on one side of the resonator as depicted in FIG. 1A (e.g., the side that contacts fluid), but it may be used on both sides as depicted in FIG. 1B, e.g., to preserve symmetry and/or to further constrain the motion of the structure to the mode of interest.

Thus, embodiments of the present invention include MEMS in-plane resonators with closed nodal anchors along a closed nodal path on any surface or surfaces of a resonant mass. Such a closed nodal anchor can be used to form a partially or fully enclosed cavity (or cavities) in which other MEMS structures can be provided, as discussed more fully below. Even for applications where partial encapsulation is not needed, a closed loop anchor provides symmetry and may help suppress spurious vibration modes. As discussed more fully below, such MEMS in-plane resonators with closed nodal anchors may be employed in any of a variety of applications, such as, for example, resonator applications (e.g., biosensing and other sensing applications), oscillators, filters, gyroscopes, etc.

FIG. 1 schematically shows two anchoring strategies in accordance with exemplary embodiments of the present invention. For the sake of simplicity here, other components, such as drive and sense electrodes, are omitted.

Figure 1B:
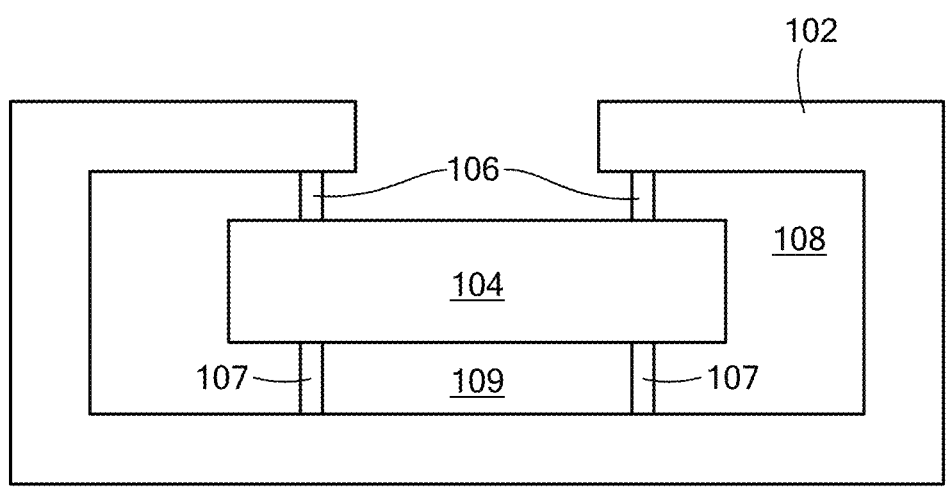

FIG. 1A schematically shows a cross-sectional side view of a device anchored at the fluid-contacting surface. Among other things, the device includes a substrate 102, a resonant mass 104, and a closed nodal anchor 106 at the (top) fluid-contacting surface. These structures essentially create two separate volumes, an interior cavity 108 bounded by the inside walls of the substrate 102, the closed nodal anchor 106, and the inward-facing surfaces of the resonant mass 104, while the outward-facing surface of the resonant mass 104 bounded by the closed nodal anchor 106 (which may be referred to hereinafter as the "ambient interface") is exposed to the surrounding environment (e.g., gas, liquid, or vacuum). Part or all of this exposed surface may include features to affect interaction with the external environment, as discussed further below. Structures such as drive and sense electrodes are typically located within the cavity 108.

FIG. 1B schematically shows a cross-sectional side view of a device anchored from both sides. In addition to the elements depicted in FIG. 1A, this device includes a bottom-side closed nodal anchor 107 coupled to the bottom surface of the resonant mass 104 and the floor of the substrate 102, e.g., to preserve symmetry and/or to further constrain the motion of the structure to the mode of interest. The bottom-side closed nodal anchor 107 essentially creates two interior cavities, a cavity 108 outside the perimeter of the closed nodal anchor 107 and a cavity 109 inside the perimeter of the closed nodal anchor 107. Structures such as drive and sense electrodes may be located within the cavity 108 and/or the cavity 109.

It should be noted that in embodiments of the type shown in FIGS. 1A and 1B, the resonant mass 104 is recessed below the upper surface of the substrate 102, and the resulting fluid volume may be used to receive a fluid to be acted upon by the resonant mass 104 as discussed further below, although the resonant mass 104 need not be recessed below the upper surface of the substrate 102.

It should be noted that the substrate 102, while shown as a unitary structure, may be composed of multiple layers and/or interconnected structures, e.g., formed using various MEMS fabrication processes including micromachining and wafer-to-wafer bonding.

The cavity 108 is typically hermetically sealed and typically houses various components such as, for example, electrical and mechanical components used to drive and sense the motion of the resonant mass in the contour mode (e.g., capacitive/electrostatic transducers and/or piezoelectric transducers). For convenience, such structures are not shown in FIG. 1 but are discussed further below. Embodiments of the present invention generally enable such transducers to be used in liquid or harsh environments without degrading the transduction. It should be noted that, in addition to housing the drive and/or sense transducers for the resonant mass, the sealed cavity also tends to reduce the overall damping of the device (particular in embodiments in which the cavity is evacuated) and also prevents contaminants (including bubbles) from getting underneath the resonator and affecting its performance.

Various embodiments of the present invention may be fabricated using conventional surface micromachining techniques and high-volume wafer fabrication processes, widespread for fabricating MEMS sensors, to construct in-plane resonators exposed to an external environment with hermetically isolated transducers. Such a high-volume process also enables arrays of sensors to be fabricated on the same centimeter- or millimeter-scale chip with optionally integrated electronics, providing generally better selectivity and robustness as well as enhanced algorithms for signal conditioning. Thus, embodiments of the present invention may include MEMS in-plane resonators smaller than a few centimeters across and less than a few millimeters thick, allowing such device to be fabricated in large volumes and enabling their use in applications where small size is necessary or desirable.

Thus, embodiments include a bulk acoustic wave device designed to resonate predominately in the lateral (in-plane) direction. The underside, edges, and part of the top surface of the resonant element are isolated, e.g., with a hermetic vacuum seal, to allow actuation and sensing with minimal damping, with the rest of the top surface in contact with a viscous medium such as water. The actuation and sensing may be done using electrostatic, piezoelectric, or other types of transducers. The seal also serves as the anchor that connects the sensor to the substrate and occurs along a closed nodal path of minimum displacement. The lateral motion of the device minimizes viscous damping, enabling applications in viscometry, chemical and biological sensing based on mass or stress, densitometry, thermometry, and pressure sensing. The isolated electronics allow for superior robustness. Furthermore, by preventing the liquid from entering any gaps around the device, bubble formation and particle trapping are reduced or eliminated.

It should be noted that the resonant mass 104 is not limited to any particular shape. Generally speaking, the resonant mass 104 can be any shape defined in two dimensions, e.g. a circle, square, rectangle, ring, etc. The thickness dimension can be constant or can vary across the structure.

Figure 2A:
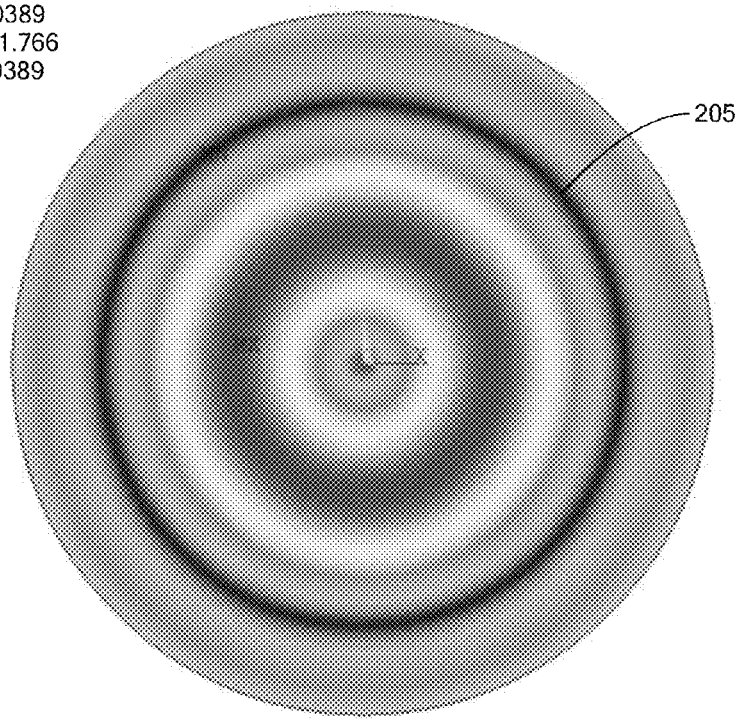
FIG. 2A shows an example contour mode shape for a circular disk resonant mass operating in a second order breathing mode and FIG. 2B shows an exemplary closed nodal path for the circular disk resonant mass along which the anchor would be placed, in accordance with an alternate embodiment of the present invention.
Figure 2B:
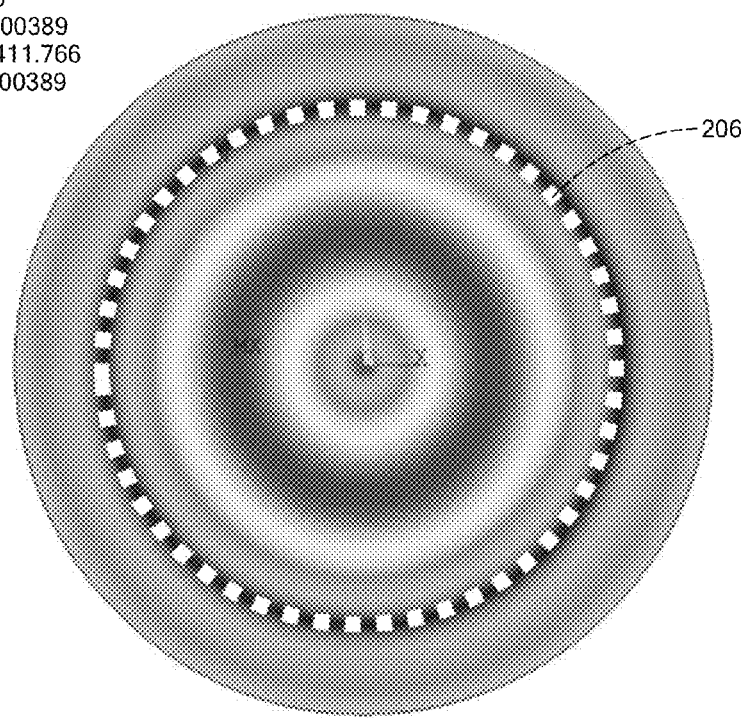

FIG. 2A shows an example contour mode shape for a circular disk resonant mass operating in a second order breathing mode. The contour is plotted as the magnitude of displacement such that nodes exist in the region 205. FIG. 2B shows an exemplary closed nodal path 206 for the circular disk resonant mass along which the anchor would be placed. Thus, in this example, the anchor is a concentric ring extruded out of the plane (or into the plane) of the contour attached to the closed nodal path. As mentioned above, the anchor should be as narrow as possible since the true nodal path is infinitely thin.

Figure 3A:
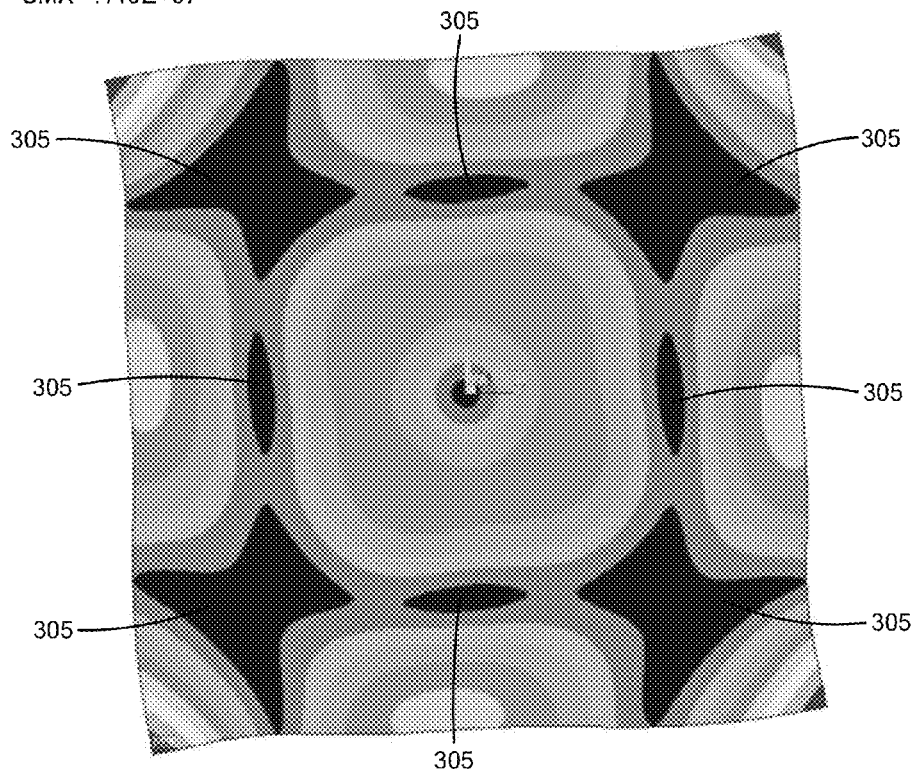
FIG. 3A shows an example contour mode shape for a square plate resonant mass operating in a second order breathing mode and FIG. 3B shows an exemplary closed nodal path for the square plate resonant mass along which the anchor would be placed, in accordance with an alternate embodiment of the present invention.
Figure 3B:
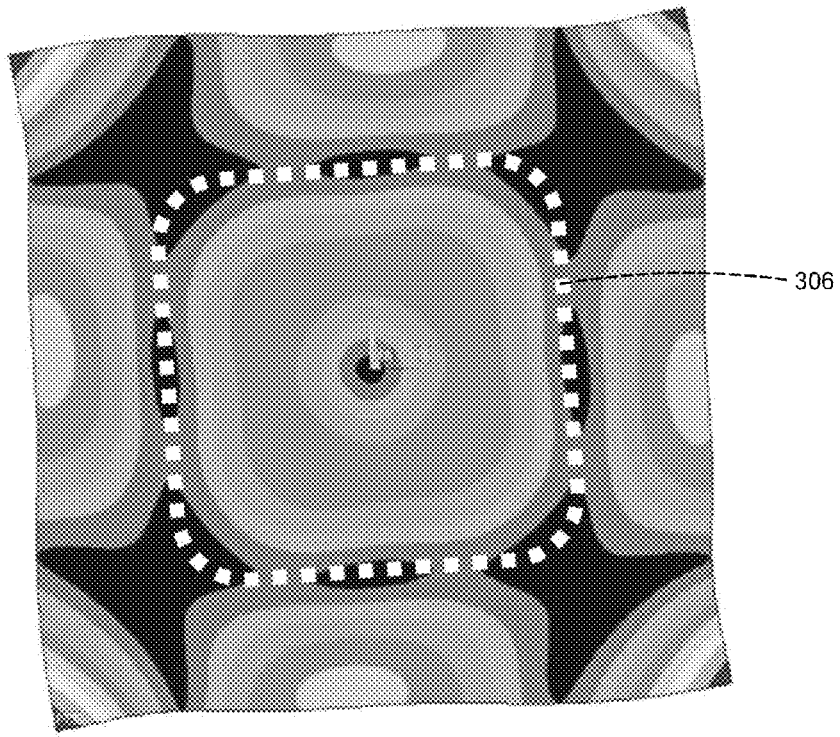

FIG. 3A shows an example contour mode shape for a square plate resonant mass operating in a second order breathing mode. The contour is plotted as the magnitude of displacement such that nodes exist in the regions 305. FIG. 3B shows an exemplary closed nodal path 306 for the square plate resonant mass along which the anchor would be placed. The closed nodal path 306 includes points that have non-zero displacement, but the closed nodal path 306 is defined by local minima in displacement so as to form a substantially square closed loop.

Once anchored, the area within the closed nodal path can define the fluid volume, while the outer edge and/or back side of the resonant mass can be used for electromechanical drive and sense. In an exemplary embodiment shown in FIG. 1, the anchor essentially hangs from the underside of the top of the substrate 102 to completely prevent fluid from reaching the cavity 108.

FIGS. 4A and 4B schematically show a top perspective view and a cross-sectional side view (taken along line 402) of a device having a circular disk resonant mass, in accordance with an exemplary embodiment of the present invention. As shown in FIG. 4A, a recessed cavity is formed at the top of the device, e.g., to allow the external environment (e.g., fluid) to interact with the top surface of the sensor. FIG. 4B shows the isolated transducer volume 108 formed at least in part by the resonant mass, the closed nodal anchor 106, and the substrate. For convenience, sense/drive electrodes are not shown in these figures.

Embodiments of the present invention may be formed using conventional surface micromachining techniques such as lithography, film deposition, and selective etching, all widespread for fabricating MEMS sensors, to construct a resonant sensor.

FIGS. 5 and 6 schematically show the types of processes that may be involved with forming the substrate, anchor, and resonant mass for devices of the type described above. It should be noted that the various structures that may be included within the cavity, such as drive and sense electrodes and structures formed on the resonant mass to interact with the drive and/or sense electrodes, are not represented in these exemplary process flows. Such structures (which are discussed further below) generally would be formed along with the structures shown.

It should be noted that the exemplary process flows described below are conceptual and the present invention is not limited to any particular fabrication process. In practice, some of the process steps described below may be modified or omitted, and additional process steps may be included. For example, patterning of a particular material or otherwise forming a material layer may involve deposition of additional materials (e.g., etch stop materials, photoresist materials, and/or passivation materials, etc.) and may involve subsequent removal of some or all of the additional materials (e.g., by etching, grinding, etc.).

FIG. 5 is a conceptual process flow of a MEMS fabrication process for producing a MEMS in-plane resonator of the type shown in FIG. 1A, in accordance with a first exemplary embodiment of the present invention.

Figure 5A:
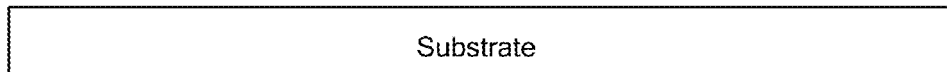
FIGS. 5A-5O schematically show a conceptual process flow of a MEMS fabrication process for producing a MEMS in-plane resonator of the type shown FIGS. 6A-6K schematically show a conceptual process flow of a MEMS fabrication process for producing a MEMS in-plane resonator of the type shown in FIG. 1A from the top down allowing for fluid contact from the bottom, in accordance with a second exemplary embodiment of the present invention.
Figure 5B:
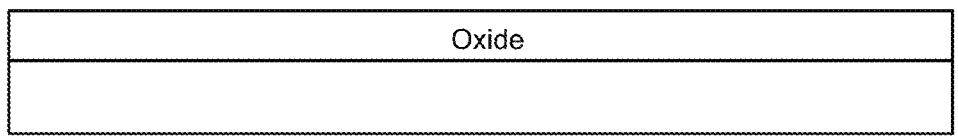

Beginning with a substrate (e.g., silicon or polysilicon) in FIG. 5A, an oxide layer is formed as shown in FIG. 5B. The oxide layer may be formed, for example, by deposition or using a thermal oxidation process.

Figure 5C:

In FIG. 5C, the oxide layer is patterned to provide openings through which the side walls of the substrate 102 will be formed.

Figure 5D:
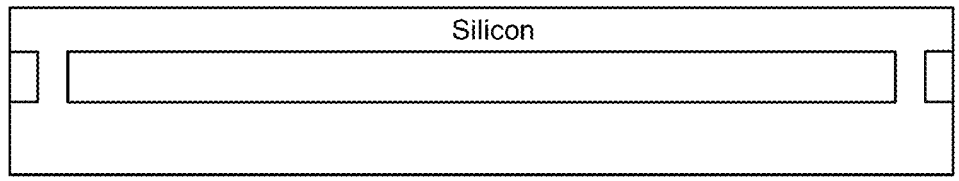

In FIG. 5D, silicon (typically polysilicon) is deposited so as to fill the openings and form a silicon device layer.

Figure 5E:
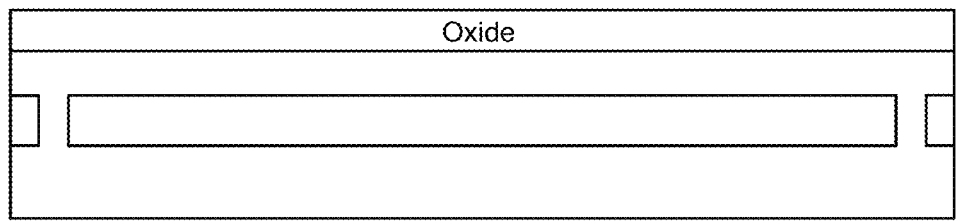

In FIG. 5E, a second oxide layer is deposited or grown on the silicon layer.

Figure 5F:
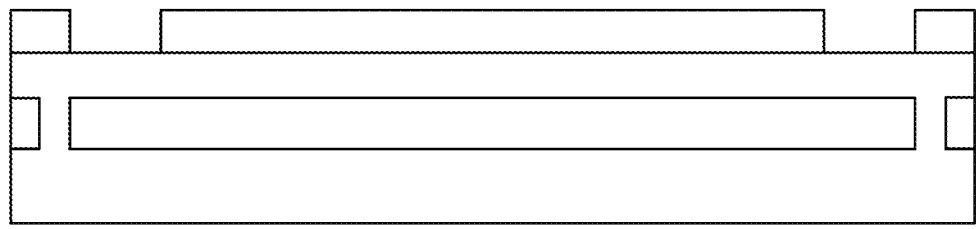

In FIG. 5F, the second oxide layer is patterned to form openings where the silicon layer will be etched.

Figure 5G:
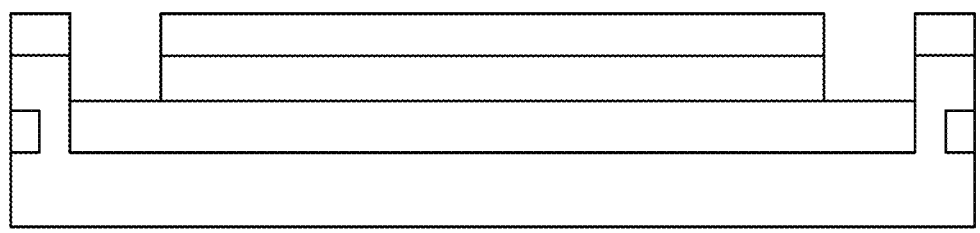

In FIG. 5G, the silicon layer is etched through the openings in the second oxide layer to form the resonant mass.

Figure 5H:
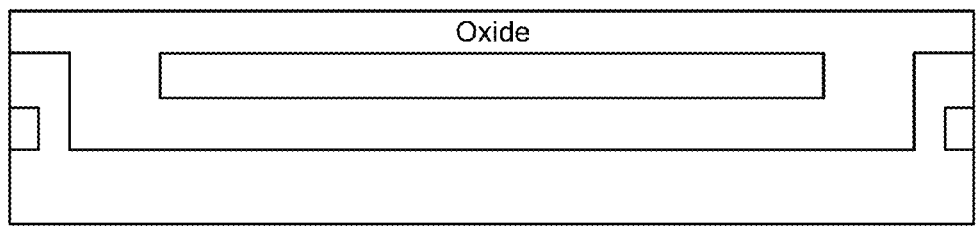

In FIG. 5H, oxide is deposited to fill the spaces around the resonant mass.

Figure 5I:
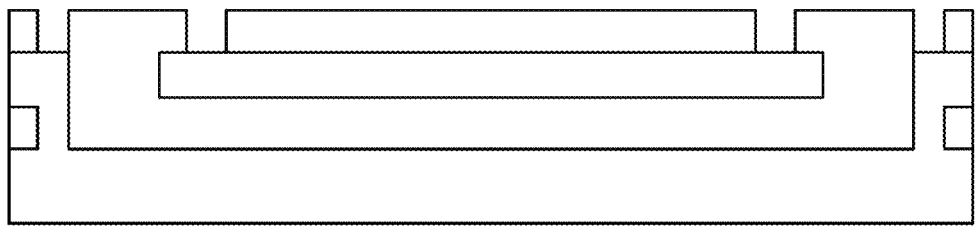

In FIG. 5I, the top oxide layer is patterned to expose areas of the silicon layer where the side walls are to be extended and where the anchor is to be formed.

Figure 5J:
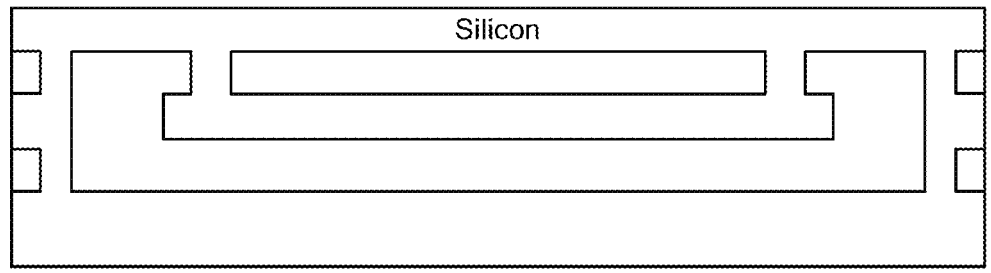

In FIG. 5J, silicon (typically polysilicon) is deposited to fill the openings in the top oxide layer.

Figure 5K:
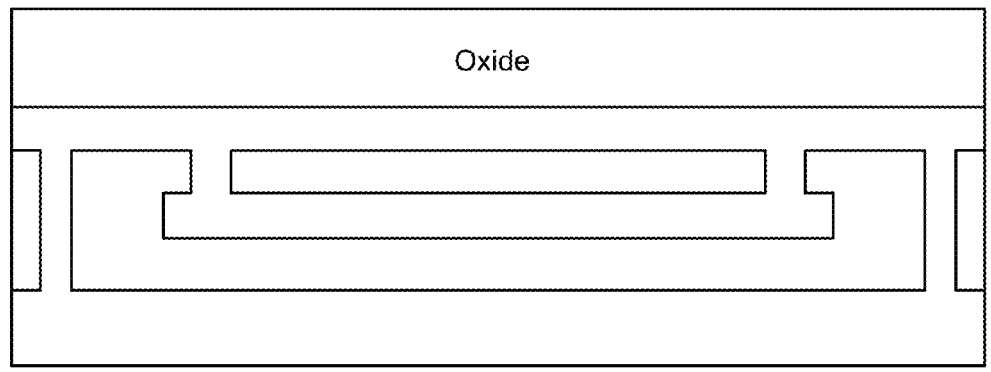

In FIG. 5K, another oxide layer is deposited or grown.

Figure 5L:
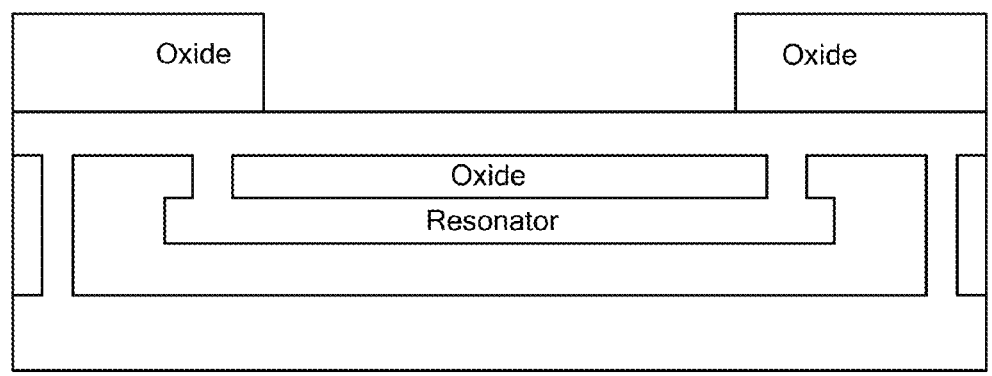

In FIG. 5L, the top oxide layer is patterned to expose the portion of the silicon layer that will be removed.

Figure 5M:
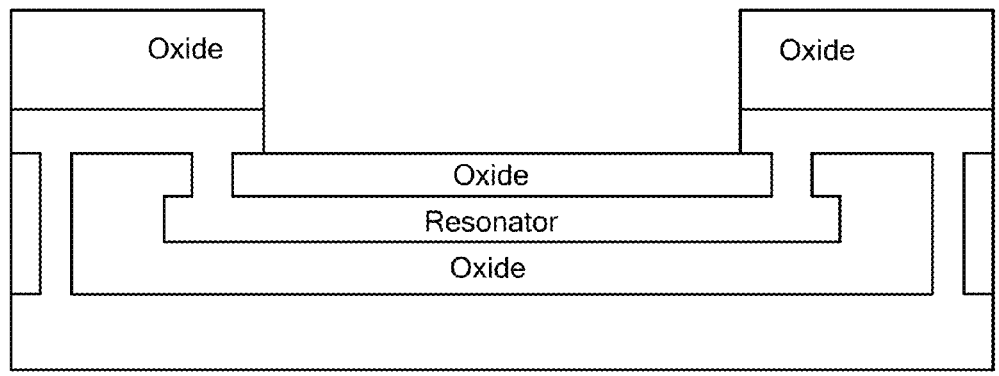

In FIG. 5M, the silicon layer is etched through the opening in the top oxide layer.

Figure 5N:
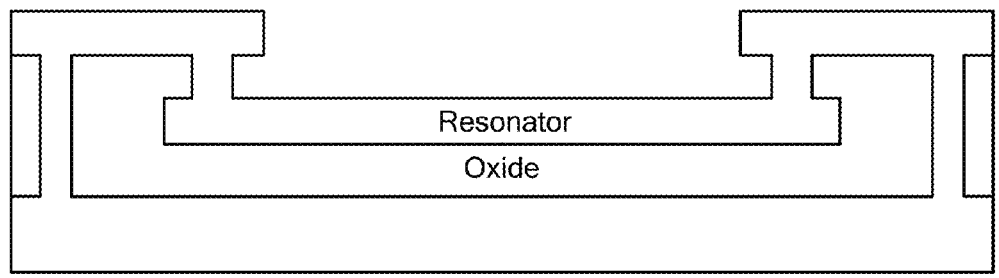

In FIG. 5N, the remainder of the top oxide layer is removed. This exposes the top ambient interface of the resonant mass.

Figure 5O:
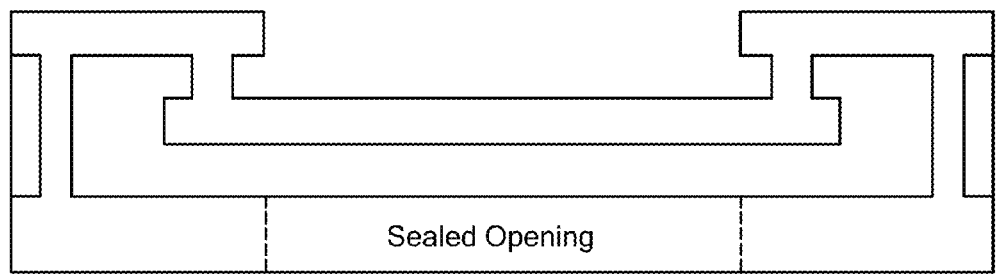

In FIG. 5O, one or more openings are formed through the bottom of the substrate 102 to expose the oxide in the cavity 108, the oxide is removed (e.g., using dry, wet, or vapor HF etching) to "release" the resonant mass, and the openings are filled or otherwise sealed. The cavity 108 may be evacuated or filled with a gas prior to sealing.

The exemplary process flow shown in FIG. 5 essentially builds the resonator from the bottom up. FIG. 6 is a conceptual process flow of a MEMS fabrication process for producing a MEMS in-plane resonator of the type shown in FIG. 1A from the top down, in accordance with a second exemplary embodiment of the present invention.

Figure 6A:
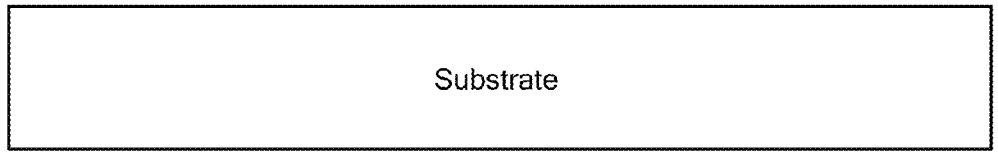
Figure 6B:
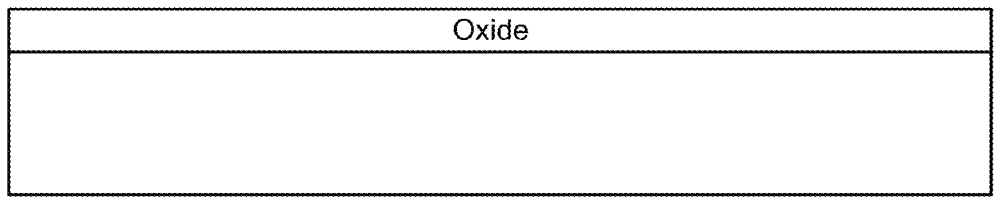

Beginning with a substrate (e.g., silicon or polysilicon) in FIG. 6A, an oxide layer is formed as shown in FIG. 6B. The oxide layer is formed, for example, by deposition or using a thermal oxidation process.

Figure 6C:
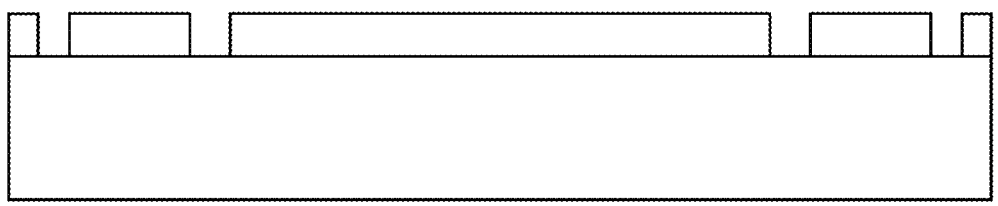

In FIG. 6C, the oxide layer is patterned to provide openings through which the side walls of the substrate 102 and anchors will be formed.

Figure 6D:
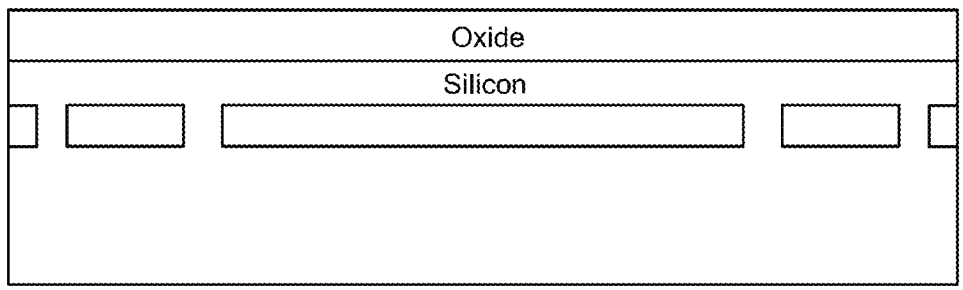

In FIG. 6D, silicon (typically polysilicon) is deposited so as to fill the openings and form a silicon device layer, and a second oxide layer is grown or deposited.

Figure 6E:
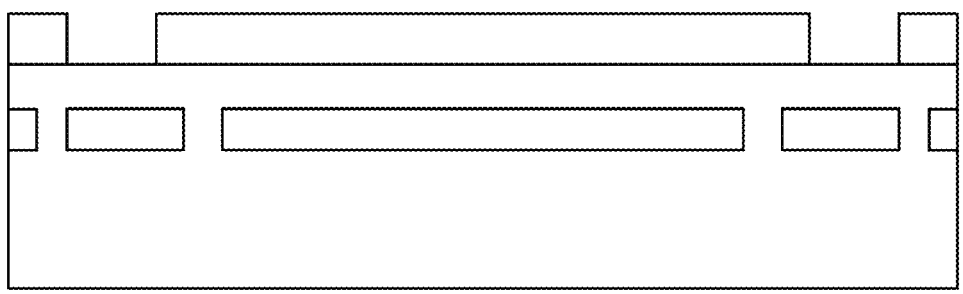

In FIG. 6E, the second oxide layer is patterned to form openings where the silicon or polysilicon layer will be etched.

Figure 6F:
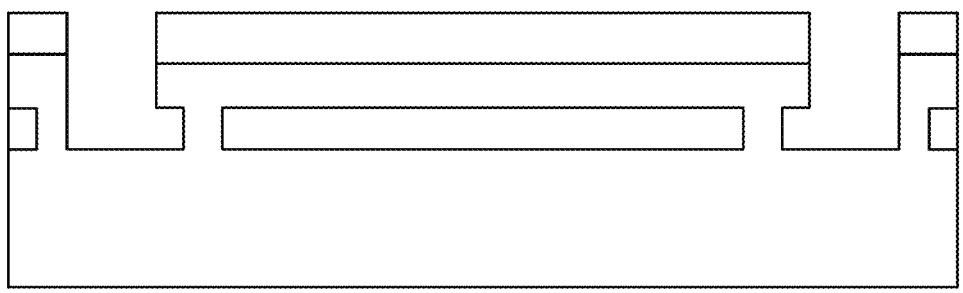

In FIG. 6F, the silicon layer is etched through the openings in the second oxide layer to form the resonant mass.

Figure 6G:
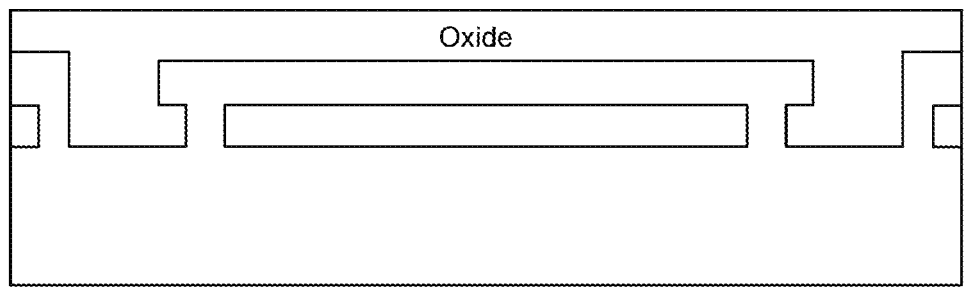

In FIG. 6G, oxide is deposited to fill the spaces around the resonant mass.

Figure 6H:
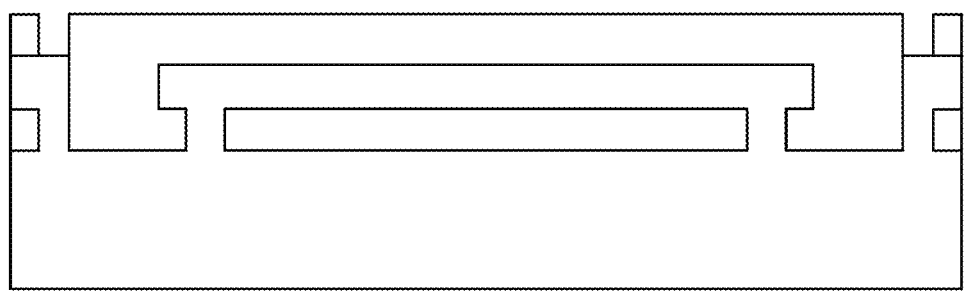

In FIG. 6H, the top oxide layer is patterned to expose areas of the silicon layer where the side walls are to be extended.

Figure 6I:
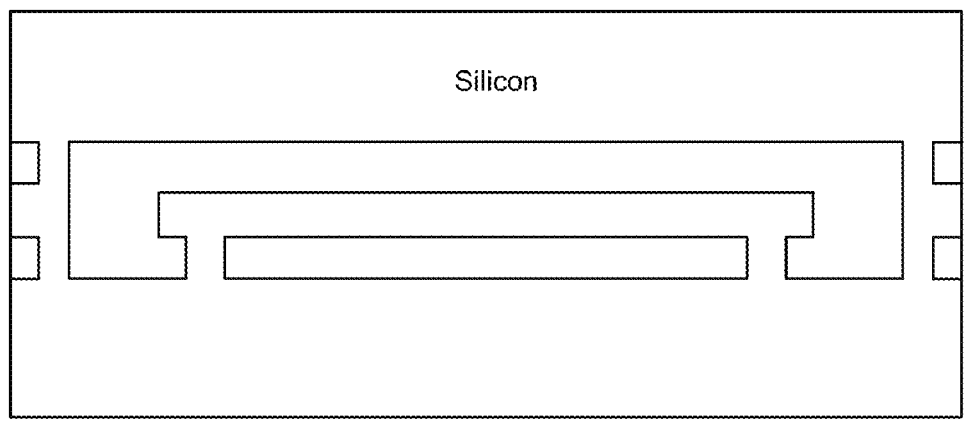

In FIG. 6I, silicon or polysilicon is deposited to fill the openings in the top oxide layer and to form the bottom of the device.

Figure 6J:
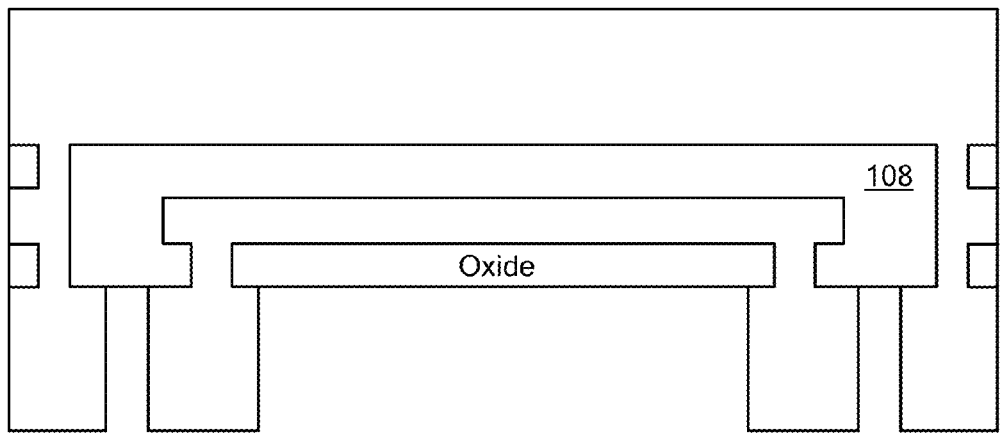
Figure 6K:
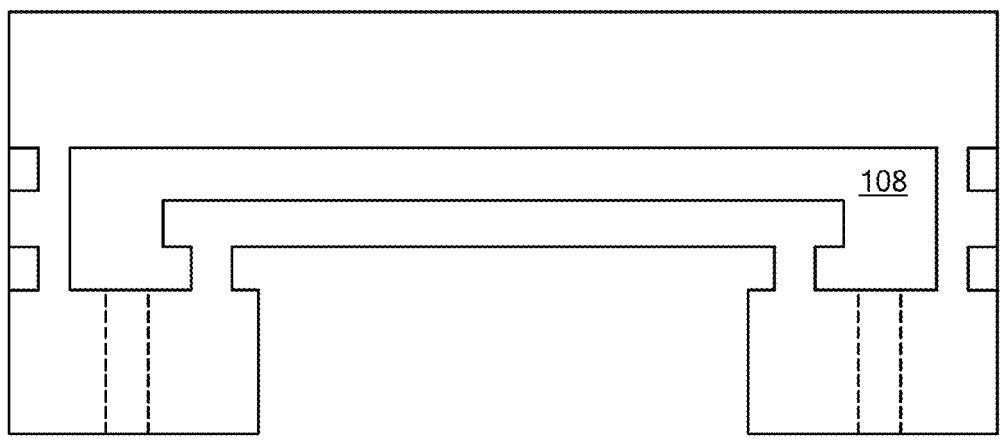

In FIG. 6J, one or more openings are formed by etching through the bottom of the substrate 102 (and optionally through the top silicon layer) to expose the oxide in the cavity 108 as well as the oxide underlying the resonant mass, the oxide is removed (e.g., using dry, wet, or vapor HF etching) to "release" the resonant mass, and the openings to the cavity 108 are filled or otherwise sealed. The cavity 108 may be evacuated or filled with a gas prior to sealing. The resulting device is shown in FIG. 6K.

It should be noted that there are many well-developed approaches known to those skilled in the art to accomplishing the sealing of the cavity following release of the resonant mass, including capping one side of the sensor with another wafer after release or depositing material to seal etch holes.

Also, the described processes may be adapted to use other materials and may be adapted to start with a silicon-on-insulator wafer that includes an oxide layer enclosed between two silicon layers. As known to those skilled in the art, anchoring on an SOI wafer may be done to a structure in the same plane as the mass or in a direction normal to this plane. Also, as discussed in more detail below, the resonator cap may be formed from a separate wafer and bonded to the substrate wafer using any of a variety of wafer-to-wafer bonding techniques.

As discussed above, the cavity 108 is typically hermetic and typically houses various components such as, for example, electrical and mechanical components used to drive and sense the motion of the resonant mass in the contour mode (e.g., capacitive/electrostatic transducers and/or piezoelectric transducers).

Figure 7:
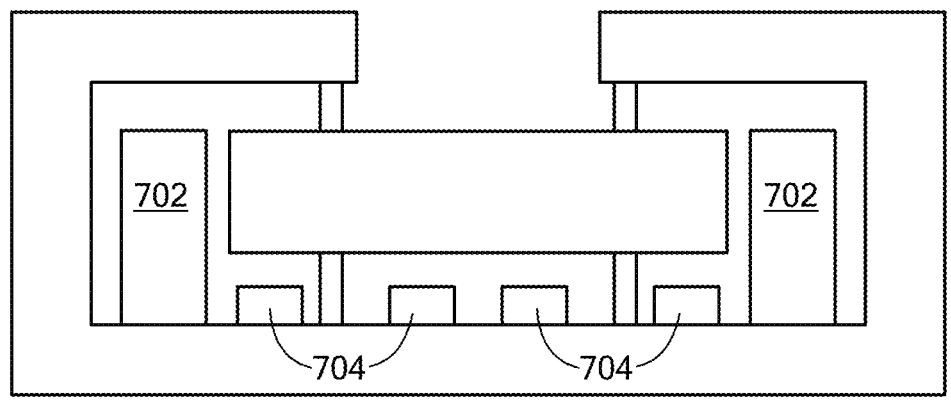
FIG. 7 schematically shows an exemplary configuration in which electrostatic drive electrodes and sense electrodes are formed on the bottom substrate that underlies the resonant mass, in accordance with a first exemplary embodiment of the present invention.

FIG. 7 schematically shows an exemplary configuration in which electrostatic drive electrodes 702 and sense electrodes 704 are formed on the bottom substrate that underlies the resonant mass, in accordance with a first exemplary embodiment of the present invention.

Figure 8:
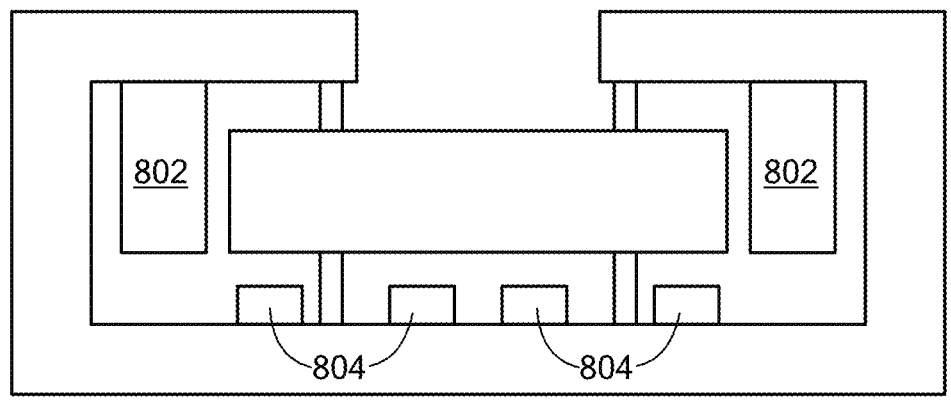
FIG. 8 schematically shows an exemplary configuration in which electrostatic drive electrodes are formed on the top substrate along with the anchor, and sense electrodes are formed on the bottom substrate that underlies the resonant mass, in accordance with a second exemplary embodiment of the present invention.

FIG. 8 schematically shows an exemplary configuration in which electrostatic drive electrodes 802 are formed on the top substrate along with the anchor, and sense electrodes 804 are formed on the bottom substrate that underlies the resonant mass, in accordance with a second exemplary embodiment of the present invention.

Figure 15:
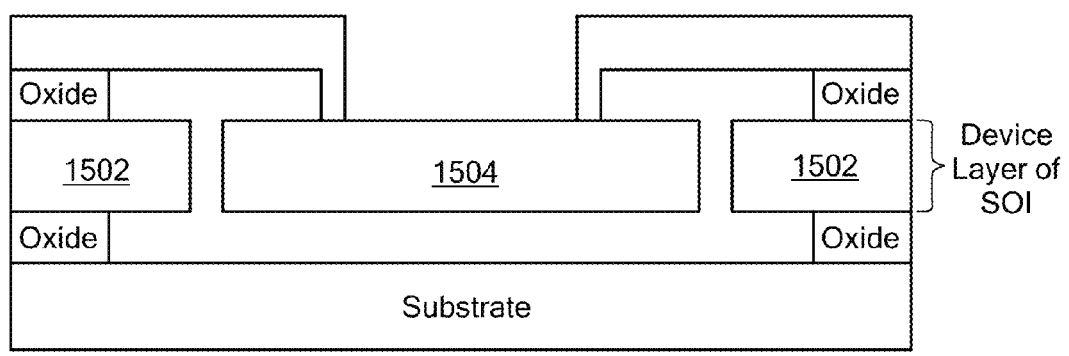
FIG. 15 schematically shows an exemplary configuration in which electrostatic drive electrodes extend from the side of the device, e.g., formed along with the resonant mass from the device layer of an SOI wafer, in accordance with a third exemplary embodiment of the present invention.

FIG. 15 schematically shows an exemplary configuration in which electrostatic drive electrodes 1502 extend from the side of the device, e.g., formed along with the resonant mass 1504 from the device layer of an SOI wafer. The drive electrodes 1502 are isolated from the top and bottom of the substrate by oxide spacers (where the oxide between the electrodes 1502 and the bottom substrate is from the oxide layer of the SOI wafer, and the oxide between the electrodes 1502 and the top is formed during fabrication of the device).

It should be noted that the sense structures (e.g., sense electrodes 704 shown in FIG. 7, sense electrodes 804 shown in FIG. 8) typically would be located adjacent to areas of the resonant mass with greatest displacement, which for a circular disk resonant mass is approximately halfway between the anchor and the center of the disk and for a square plate resonant mass is at the corners of the plate.

In the exemplary embodiments shown in FIGS. 7 and 8, the drive electrodes are placed along the edge of the resonant mass and are used to resonate the resonant mass in the contour mode. While two drive electrodes are shown in the cross-sectional views, embodiments may include more than two drive electrodes or may include a single drive electrode (e.g., completely surrounding the resonant mass). Similarly, while the sense electrodes are shown in pairs, other configurations may be employed.

Figure 13:
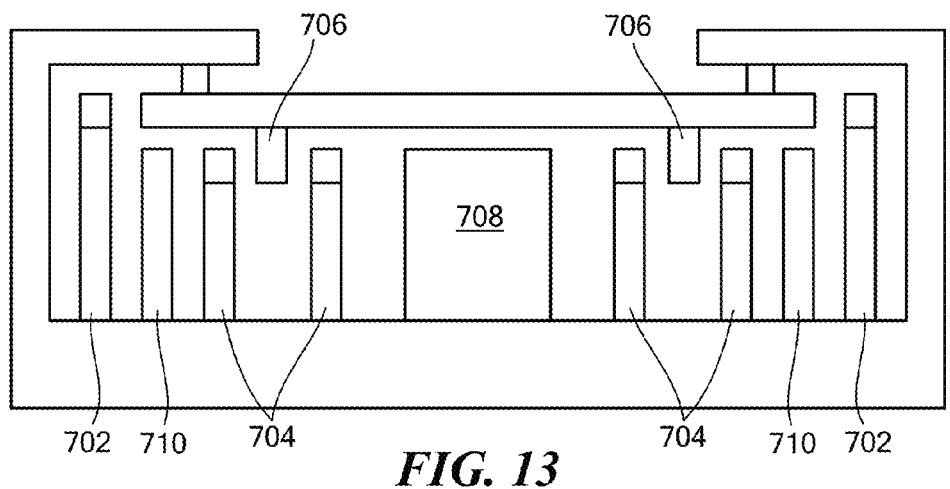
FIG. 13 schematically shows a configuration of electrodes similar to those shown in FIG. 7 with additional structures including protrusions and shield structures, in accordance with an alternative embodiment of the present invention.
Figure 14:
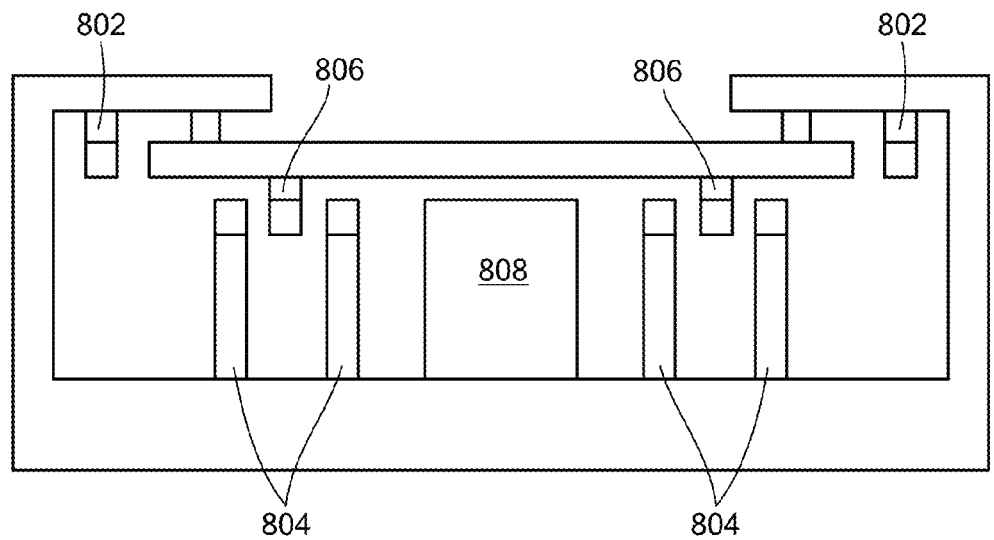
FIG. 14 schematically shows a configuration of electrodes similar to those shown in FIG. 8 with additional structures including protrusions and shield structures, in accordance with an alternative embodiment of the present invention.

It should be noted that the present invention is not limited to the types of drive and sense structures shown in FIGS. 7 and 8 and may include other types of structures, such as passive shield structures (e.g., a shield structures 708 and 808 shown respectively in FIGS. 13 and 14 may be placed between the innermost sense electrodes, shield structures 710 shown in FIG. 13 may be placed between the drive and sense electrodes, protruding structures 706 and 806 shown respectively in FIGS. 13 and 14 may be included on the underside of the resonant mass to interact with the corresponding sense electrodes for sensing resonance of the resonant mass and more specifically for detecting changes in the resonance frequency of the resonant mass due to changes in effective mass or other effects as the resonant mass interacts with the external environment). As discussed above, different materials and transduction mechanisms may be employed, including piezoelectric (AlN, ZnO, quartz, etc.) and capacitive (Si, metal, diamond, etc.) transduction.

For convenience, various structures are not shown in FIGS. 7, 8, 13, 14, and 15 such as, for example, electrical connections to the drive electrodes, sense electrodes, and perhaps other structures. The present invention is not limited to any particular types or placement of transducers and other structures.

In the exemplary embodiments described above, particularly with reference the fabrication process of FIGS. 5 and 6, the substrate top including anchor and resonant mass is formed in situ as part of the wafer fabrication process. In certain alternative embodiments, these structures may be formed from a separate wafer and bonded to a substrate wafer using any of a variety of wafer-to-wafer bonding techniques (e.g., glass seal, metal-to-metal, etc.).

Figure 9:
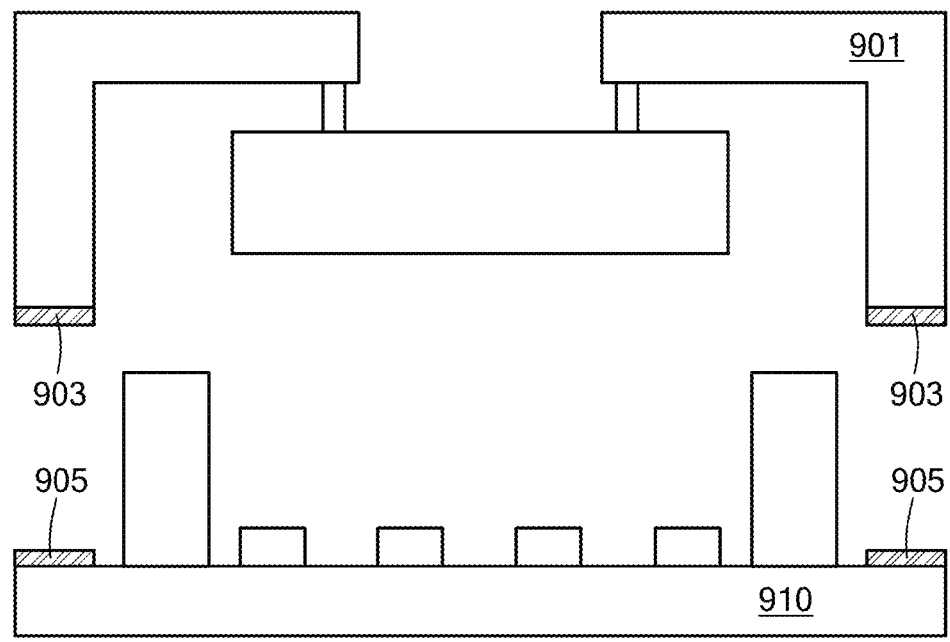
FIG. 9 schematically shows a wafer capping embodiment, in accordance with an exemplary embodiment of the present invention.

FIG. 9 schematically shows a wafer capping embodiment, in accordance with an exemplary embodiment of the present invention. Here, top (cap) portion of the device 901 including part of the substrate, the anchor, and the resonant mass is formed from a first wafer separate from the substrate wafer 910, which in this example includes drive and sense electrodes similar to the configuration shown in FIG. 7. The two wafers are bonded to one another to produce the MEMS in-plane resonator with isolated cavity encapsulating the various drive, sense, shield, and other structures. In certain embodiments, the top portion 901 and/or the bottom portion 910 may include appropriate bonding materials (e.g., glass frit, solder, metallization, etc.) to facilitate or enable the wafer-to-wafer bonding. In the exemplary embodiment shown in FIG. 9, the top portion 901 includes a bonding material 903 on the bottom of the side walls and the bottom portion 910 includes a bonding material 905 at the locations where bonding will occur. It should be noted that the bonding materials 903 and 905 may be the same material or may be different materials. It should be noted that the bond formed between the portions 901 and 910 is typically hermetic, although in alternative embodiments, a non-hermetic bond may be sealed, for example, by applying a hermetic material over the bond site.

Figure 10:
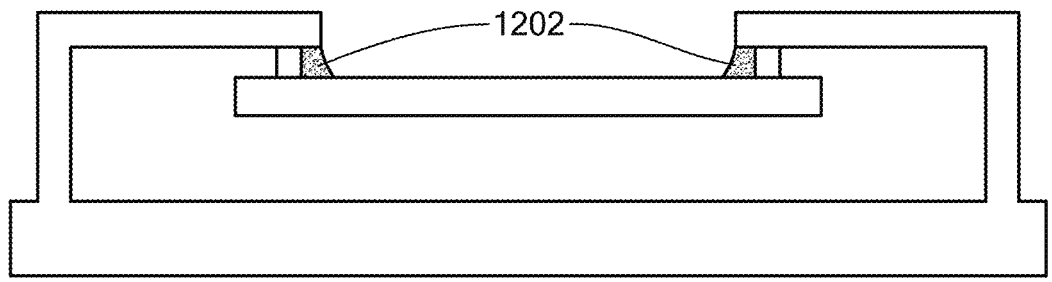
FIG. 10 schematically shows an embodiment in which a recess along the outer edge of the closed nodal anchor is filled with a material, in accordance with an alternate embodiment of the present invention.

In the type of embodiment shown in FIG. 1, the substrate 102 overhangs the outer edge of the closed nodal anchor to form a recess. It should be noted that the device may be formed without such an overhang. Alternatively, the recess may be partially or completely filled with a material 1202, as depicted in FIG. 10. The material 1202 may be, for example, an elastic material or a sealant material, e.g., to seal or further seal the anchor itself and/or the interfaces between the anchor and the substrate and/or resonant mass. The filler material may be provided in order to reduce or prevent particles from becoming caught in the recess or bubbles from forming in the recess.

Figure 11:
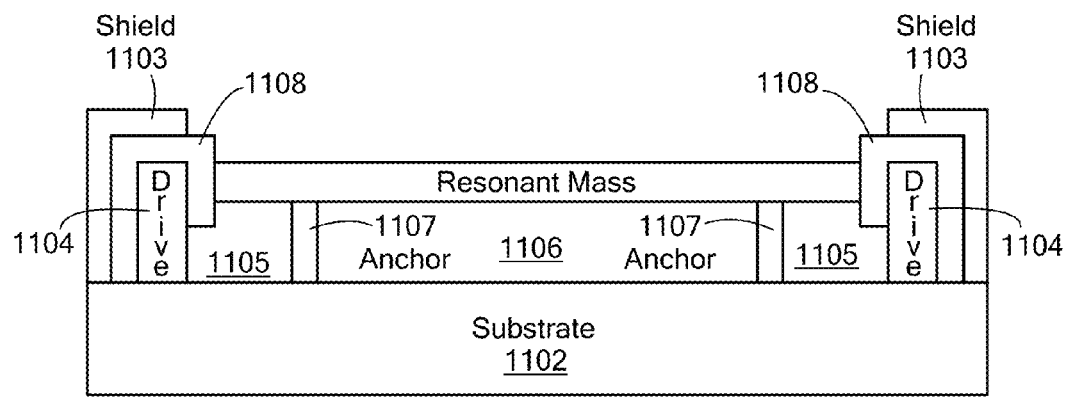
FIG. 11 is a schematic diagram showing a cross-sectional side view of a lateral resonator in accordance with an alternate embodiment of the present invention.

FIG. 11 is a schematic diagram showing a cross-sectional side view of a lateral resonator in accordance with an alternate embodiment of the present invention. Here, the resonant mass 1101 is anchored to the substrate 1102 by a closed nodal anchor 1107, forming a cavity 1106 that may be used to house various structures isolated from the outside environment. Drive electrodes 1104 (and perhaps other structures) are placed outside of the cavity 1106, but the drive electrodes are isolated from the external environment using an elastic plug 1108 formed over the exposed portions of the electrodes 1104 and a shield 1103 (e.g., of a silicon-based material) is formed over a portion of the elastic material 1108 so as to support and protect the underlying elastic material 1108 while still allowing for movement of the resonant mass 1101. The elastic plug

1108 and shield 1103 form a second sealed cavity 1105. Sense electrodes and other structures may be located within the cavity 1105 and/or within the cavity 1106.

Embodiments of the present invention may be used for a variety of applications, including, among others, liquid applications (e.g., viscometry, densitometry, biological/chemical sensing) and gas sensing applications (e.g., radon, carbon monoxide, smoke, etc., where a polymer or other film may be added to the sensor surface to further degrade damping performance), oscillators, gyroscopes, filters, etc. Bulk acoustic wave resonators are particularly well-suited to mass-based sensing (e.g., biosensing) applications because they tend to have very high resonant frequencies and stiffness compared to flexural modes, but can have comparable effective masses. Therefore, they generally have very high sensitivity to surface mass changes and good mechanical robustness. Since Q usually increases with frequency, they tend to have higher Q's and lower phase noise, as well. Contour modes tend to further increase Q by shearing the viscous medium instead of moving normal to it.

Figure 12:
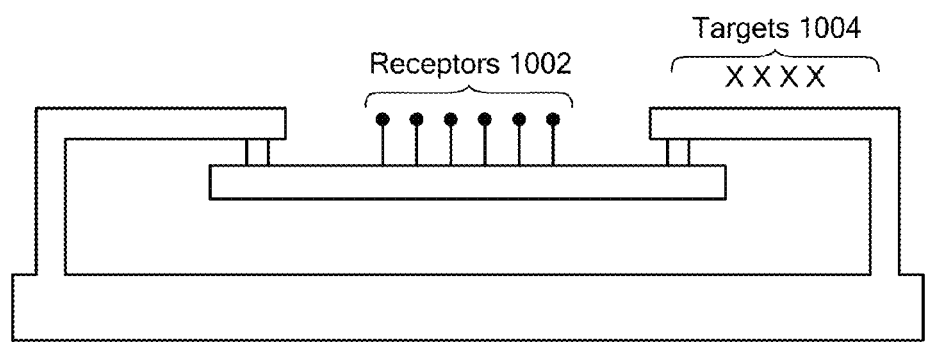
FIG. 12 schematically shows the surface of the resonant mass partially or completely coated with a material that interacts with a specific substance in the environment, in accordance with an alternate embodiment of the present invention.

As shown in FIG. 12, the surface of the resonant mass may be partially or completely coated with a material 1002 that interacts with a specific substance in the environment (e.g., a specific chemical, particulate matter, etc.). For example, the material 1002 may be designed to bind with a specific target (e.g., ligand) 1004 that, when present in sufficient quantities in the external environment, bind to the receptor material 1002 so as to increase the effective moving mass of the resonator and consequently decrease the resonance frequency of the resonator. Similarly, the material 1002 may be designed to dissolve or dissipate in the presence of a target (e.g., moisture, acid, etc.) so as to decrease the effective moving mass of the resonator and consequently increase the resonance frequency of the resonator. Such changes in resonance frequency from an increase or decrease in resonating mass can be detected and used to determine the presence and/or amount of a particular target.

Additionally or alternatively, the surface of the resonant mass and/or other exposed surfaces may be partially or completely coated with materials to increase or reduce certain interactions with the external environment, such as, for example, a passivation material (e.g., to prevent damage from exposure to certain chemicals, radiation, etc.), an anti-stiction material, a hydrophilic material, a hydrophobic material, an electrical conductor or insulator material, a chemically or electrochemically active material, an adhesive material (e.g., to capture particulate matter), a polymer film that further degrades the damping performance (e.g., for gas sensing applications) or other material. In certain embodiments, interactions with the ambient may produce an electrical potential that can be sensed using appropriate sense electronics (e.g., a potentiometer).

In embodiments that include a material on the outer surface of the resonant mass, an intermediate material layer may be included between the surface material and the underlying resonant mass. For example, the intermediate layer may include an electrical insulator material, a passivation material, or other material.

In certain embodiments, raised and/or recessed features may be patterned or otherwise formed on or from the outer surface of the resonant mass, for example, to increase the surface area exposed to the external environment (e.g., to improve chemical/biological interactivity), to increase or reduce friction with the external environment (e.g., to agitate a fluid), and/or to stiffen the resonant mass. For example, the resonant mass may include corrugations, bumps, dimples, or other features.

Any materials or other features formed on the exposed surface of the resonant mass typically would be formed prior to release of the resonant mass, e.g., prior to removal of oxide or other materials supporting the resonant mass during the fabrication process.

Thus, a MEMS sensor including a closed nodal anchor typically includes, or is used in conjunction with, a drive circuit (not shown) that provides drive signals to the drive electrodes based (either directly or via a phase-locked loop) on velocity feedback signals received from the sense electrodes so as to drive the resonant mass at its resonance frequency. In exemplary embodiments of the present invention, the drive circuit is configured to detect changes in resonance frequency (e.g., by measuring resonance frequency over time and comparing the resonance frequency with a baseline resonance frequency, e.g., established during device calibration, self-test, or otherwise). Characteristics of the external environment may be inferred, for example, based on the amount of change of the resonance frequency and/or the rate of change of the resonance frequency. In certain embodiments, the drive circuit may include a temperature sensor and may use temperature measurements to compensate for changes in resonance frequency due to temperature.

Also, a MEMS sensor including a closed nodal anchor typically includes, or is used in conjunction with, a sense circuit (not shown) that senses resonance of the resonant mass and in particular sense changes in resonance frequency caused by changes in the effective mass of the resonating body due to interactions with the environment. The sensing circuit may be configured to provide an output if the resonance frequency changes by more than a predetermined amount (typically indicating that a particular substance was detected) and/or to provide an output relative to the amount of change of the resonance frequency (e.g., indicating the amount of a particular substance that was detected, viscosity, density, etc.). The present invention is not limited to the type of output provided.

As discussed above, in the type of embodiment shown in FIG. 1, the resonant mass 104 is recessed below the upper surface of the substrate 102, and the resulting fluid volume may be used to receive a fluid to be acted upon by the resonant mass 104. In essence, then, such a MEMS sensor essentially has a built-in receptacle that is particularly well-suited to fluid-testing applications, where some fluid to be tested (e.g., a bodily fluid such as blood or urine, a water sample, etc.) may be introduced into the recess (e.g., using a dropper) as opposed to, for example, placing the MEMS sensor into a container of the fluid, which also may be possible in some applications but not others. Thus, such MEMS sensors may be included in a variety of products and form factors specifically designed for fluid testing (for example, without limitation, blood tests, pregnancy tests, urinalysis, water tests, etc.). The sensing circuit of such products may be configured to provide a binary output (e.g., detected or not detected, pregnant or not pregnant, etc., using any of a variety of outputs such as an LED, LCD screen, audible beep, etc.) or to provide a relative reading (e.g., a measured concentration of the target substance). Such products may be included in kits with other components, such as a cup for collecting fluid and/or a dropper for transferring fluid to the receptacle in the product.

In certain embodiments, a predetermined electrical potential may be applied to conductive surfaces that contact the ambient such as to an outer surface of the resonant mass and/or exposed portions of the substrate (either directly or to a conductive material disposed on the outer surface of those structures). For example, a zero potential may be applied to reduce or eliminate electrochemical interactions or a non-zero potential may be applied to encourage electrochemical interactions. The electrical potential may be varied over time, for example, starting at one potential (e.g., zero potential) to run a calibration or self-test or make an initial measurement, and then changing to another potential (e.g., a non-zero potential) to make the surface electrochemically or electrostatically reactive. In certain embodiments, different electrical potentials may be applied to the outer surfaces of the resonant mass and substrate.

In addition, alternative embodiments of the present invention may include microfluidic networks (e.g., including channels, pumps, valves, etc.) and/or sensors (electronic, mechanical, chemical, biological, drug, etc.) to support lab-on-a-chip and other applications.

Notwithstanding the in-plane contour mode of operation of the resonant mass, some out-of-plane motion may be present (e.g., due to Poisson effects), which may be acceptable in some applications. Alternatively, out-of-plane movements of the resonant mass may be managed in a variety of ways. For example, electrodes on the substrate wafer underlying portions of the resonant mass may be used to sense and/or correct out-of-plane movements electrostatically or otherwise.

Out-of-plane movements caused by imperfections in the design and/or fabrication of the various resonator components (e.g., the resonant mass, the drive electrodes, etc.), which may be proportional to the displacement and/or velocity of the resonating mass, may be reduced or suppressed in a manner similar to quadrature suppression schemes used in various MEMS gyroscopes. Some examples of quadrature suppression schemes are described by Clark in U.S. Pat. No. 5,992,233 and by Geen in U.S. Pat. No. 7,032,451, each of which is hereby incorporated herein by reference in its entirety. Quadrature suppression is also discussed in Lemkin, U.S. Pat. No. 7,051,590; in Chaumet, U.S. Patent Application Publication No. 2008/0282833; and in Saukoski, M., *System and Circuit Design for a Capacitive MEMS Gyroscope*, Doctoral Dissertation, TKK Dissertations 116, Helsinki University of Technology, Espoo, Finland (2008), each of which is hereby incorporated herein by reference in its entirety.

Out-of-plane movements caused by pressure changes in the external environment may be sensed, for example, through variable capacitance between the resonant mass and one or more electrodes on the underlying substrate, and may be used, for example, to compensate for changes in resonance frequency caused by out-of-plane movements of the resonant mass (e.g., due to stiffening of the springs or elastic plugs) or to combine resonance-frequency-based sensing (e.g., for viscosity, chemical, or biological sensing) and out-of-plane sensing (e.g., for pressure sensing) into a single MEMS device. Some examples of sensing out-of-plane movements of a mass (specifically in the context of sensing out-of-plane movements of a diaphragm of a MEMS microphone) are included in commonly-owned United States patent application publication number US2006/0237806, which is hereby incorporated by reference in its entirety.

While exemplary embodiments are described above with reference to electrostatic drivers and sensors, it should be noted that the present invention is not limited to electrostatic drivers and sensors, and other types of drivers and/or sensors (e.g., piezoelectric) may be used in certain embodiments. Some examples of piezoelectric drivers and sensors for use in MEMS sensors are provided in commonly-owned U.S. patent application Ser. No. 12/208,803 (Attorney Docket No. 2550/B84), which is hereby incorporated herein by reference in its entirety.

It should be noted that a MEMS device may include two or more in-plane resonators of the type described above, for example, to provide redundancy or to sense different characteristics of the external environment. The resonators may be configured differently, e.g., one to measure viscosity and the other including a receptor material coating to sense for a particular target substance. Measurements from the resonators may be used independently or may be combined. The resonators may be mechanically coupled, electrically coupled, or both. For example, the output of a chemical or biological sensor may be based in part on a viscosity measurement from a viscosity sensor.

Thus, embodiments may include arrays of sensors of the types described herein. Sensors may be of the same or different mechanical design, functional coating, electrical connection, etc. As discussed above, embodiments of the present invention may be fabricated using conventional surface micromachining techniques and high-volume wafer fabrication processes, widespread for fabricating MEMS sensors, to construct in-plane resonators exposed to an external environment with hermetically isolated transducers. Such a high-volume process also enable arrays of sensors to be fabricated on the same centimeter- or millimeter-scale chip with optionally integrated electronics, resulting in better selectivity and robustness as well as enhanced algorithms for signal conditioning. Thus, embodiments of the present invention may include MEMS in-plane resonators smaller than a few centimeters across and less than a few millimeters thick, allowing such device to be fabricated in large volumes and enabling their use in applications where small size is necessary or desirable.

The present invention may be embodied in other specific forms without departing from the true scope of the invention. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A MEMS sensor comprising:
a substrate;
a resonant mass configured to resonate in an in-plane contour mode;
a first closed nodal anchor connecting the resonant mass to the substrate along a first predetermined closed nodal path on a first surface of the resonant mass;
a second closed nodal anchor connecting the resonant mass to the substrate along a second predetermined closed nodal path on a second surface of the resonant mass opposite the first surface; and
at least one transducer in communication with the first resonant mass for at least one of driving and sensing in-plane movement of the resonant mass, wherein at least a portion of the first surface of the resonant mass is configured for exposure to an external environment.

2. A MEMS sensor according to claim 1, wherein the at least one transducer is at least partially contained within a cavity formed at least in part by the resonant mass, the substrate, and the first closed nodal anchor.

3. A MEMS sensor according to claim 2, wherein the resonant mass is part of a cap that is attached to a substrate wafer to form thereby an isolated cavity within which the at least one transducer is at least partially contained.

4. A MEMS sensor according to claim 1, wherein the resonant mass is movably coupled to the at least one transducer via an elastic material, and wherein portions of the at least one transducer that would otherwise be exposed to the external environment are covered with at least one material to isolate those portions from the external environment.

5. A MEMS sensor according to claim 1, wherein the at least one transducer includes at least one drive transducer and at least one sense transducer, wherein the at least one drive transducer is operatively coupled to a side edge of the resonant mass and the at least one sense transducer is operatively coupled to a bottom surface of the resonant mass, the transducers isolated from the external environment.

6. A MEMS sensor according to claim 1, further comprising:
a set of shield structures on the substrate wafer.

7. A MEMS sensor according to claim 1, further comprising circuitry configured to apply a predetermined electrical potential to at least one outer conductive surface exposed to the external environment.

8. A MEMS sensor according to claim 1, wherein the resonant mass is movably coupled by a suspension.

9. A MEMS sensor according to claim 8, wherein the suspension includes an elastic plug.

10. A MEMS sensor according to claim 2, wherein the cavity contains a partial or complete vacuum.

11. A MEMS sensor according to claim 1, wherein the at least one transducer includes one of:
a capacitively-coupled transducer; and
a piezoelectrically-coupled transducer.

12. A MEMS sensor according to claim 1, wherein the portion of the first surface configured for exposure to the external environment is at least partially covered by a material meant to interact with a specific type of target in the external environment, such interaction changing the moving mass of the resonant mass so as to change the resonance frequency of the resonant mass, the sensor further including circuitry configured to detect a change in resonance frequency resulting from such interaction.

13. A MEMS sensor according to claim 12, wherein the material includes one of:
an adhesive material to which the target adheres;
a chemically or electrochemically active material;
a hydrophilic material;
a receptor material to which a specific target binds; and
a material that dissolves or dissipates in the presence of the target so as to decrease the moving mass of the resonator and consequently increase the resonance frequency of the resonator.

14. A MEMS sensor according to claim 1, wherein the portion of the first surface configured for exposure to the external environment is at least partially covered by a material meant to reduce interactions with the external environment.

15. A MEMS sensor according to claim 1, further comprising circuitry configured to sense an electrical potential caused by interaction with the external environment.

16. A MEMS sensor according to claim 1, wherein the resonant mass includes raised and/or recessed features patterned or otherwise formed on or from the top surface of the resonant mass.

17. A MEMS sensor according to claim 1, further comprising at least one of a microfluidic network and sensors.

18. A MEMS sensor comprising:
a substrate;
a plurality of resonant masses, each resonant mass configured to resonate in an in-plane contour mode and including (a) a first closed nodal anchor connecting the resonant mass to the substrate along a first predetermined closed nodal path on a first surface of the resonant mass and (b) a second closed nodal anchor connecting the resonant mass to the substrate along a second predetermined closed nodal path on a second surface of the resonant mass opposite the first surface; and
a plurality of transducers in communication with the resonant masses for at least one of driving and sensing in-plane movement of the resonant masses, wherein at least a portion of the first surface of each resonant mass is configured for exposure to an external environment.

19. A MEMS sensor according to claim 18, wherein the plurality of transducers are at least partially contained within a cavity formed at least in part by the resonant masses, the substrate, and the first closed nodal anchors.

20. A MEMS sensor according to claim 18, wherein at least one of:
the portions of the first surfaces configured for exposure to the external environment are at least partially coated with the same material;
the portions of the first surfaces configured for exposure to the external environment are at least partially coated with different materials; and
the resonant masses are mechanically coupled.

21. Apparatus comprising an array of a plurality of MEMS sensors according to claim 1.

22. Apparatus according to claim 21, wherein at least one of:
at least two sensors are of the same mechanical design;
at least two sensors are of different mechanical designs;
at least two sensors have the same functional coating;
at least two sensors have different functional coatings; and
at least two sensors are electrically coupled.

23. A method of fabricating a MEMS in-plane resonator comprising:
forming a resonant mass supported by a substrate and configured to resonate substantially in an in-plane contour mode;
forming a first closed nodal anchor connecting the resonant mass to the substrate along a first predetermined closed nodal path on a first surface of the resonant mass;
forming a second closed nodal anchor connecting the resonant mass to the substrate along a second predetermined closed nodal path on a second surface of the resonant mass opposite the first surface; and
forming at least one transducer in communication with the first resonant mass for at least one of driving and sensing in-plane movement of the resonant mass, wherein at least a portion of the first surface of the resonant mass is configured for exposure to an external environment.

* * * * *